United States Patent
Struble

(10) Patent No.: US 6,754,529 B2
(45) Date of Patent: Jun. 22, 2004

(54) COMMITTED VENTRICULAR SAFETY PACING

(75) Inventor: Chester Struble, Eijsden (NL)

(73) Assignee: Medtronic, Inc., Minneapolis, MN (US)

( * ) Notice: Subject to any disclaimer, the term of this patent is extended or adjusted under 35 U.S.C. 154(b) by 477 days.

(21) Appl. No.: 09/842,884

(22) Filed: Apr. 27, 2001

(65) Prior Publication Data

US 2002/0183794 A1 Dec. 5, 2002

(51) Int. Cl.[7] .................................................. A61N 1/18
(52) U.S. Cl. ................................ 607/9; 607/14; 607/4; 607/5
(58) Field of Search ................................ 607/9, 25, 30, 607/123, 14, 4, 5; 600/509, 508

(56) References Cited

U.S. PATENT DOCUMENTS

| | | | | |
|---|---|---|---|---|
| 5,312,450 A | * | 5/1994 | Markowitz | 607/14 |
| 5,902,324 A | * | 5/1999 | Thompson et al. | 607/9 |
| 6,070,101 A | * | 5/2000 | Struble et al. | 607/9 |
| 6,081,748 A | * | 6/2000 | Struble et al. | 607/9 |
| 6,122,545 A | * | 9/2000 | Struble et al. | 607/9 |
| 6,442,427 B1 | * | 8/2002 | Boute et al. | 607/9 |
| 6,477,415 B1 | * | 11/2002 | Yerich et al. | 607/9 |

* cited by examiner

Primary Examiner—Henry Bennett
Assistant Examiner—Fadi H. Dahbour
(74) Attorney, Agent, or Firm—Girma Wolde-Michael; Thomas F. Woods; Paul H. McDowall

(57) ABSTRACT

A method and apparatus provides a sensed AV delay and/or a paced AV delay following an atrial sensed event and/or an atrial paced event, respectively. The AV delay is a predetermined time period initiated by the respective occurrence of the atrial sensed event or atrial paced event. A ventricular safety pacing window is defined during at least an initial portion of the AV delay. Ventricular events are sensed during the AV delay. If a ventricular event is sensed during the ventricular safety pacing window, then a commitment is made to the delivery of a ventricular safety pace upon expiration of the AV delay.

53 Claims, 10 Drawing Sheets

COMMITTED VENTRICULAR SAFETY PACING

FIELD OF THE INVENTION

The present invention relates generally to implantable medical devices and methods of cardiac stimulus. More particularly, the present invention pertains to implantable medical pacing devices and methods that employ ventricular safety pacing (VSP) in cardiac stimulation.

BACKGROUND OF THE INVENTION

Generally, in the heart, the sinus (or sinoartrial (SA)) node typically located near the junction of the superior vena cava and the right atrium) constitutes the primary natural pacemaker by which rhythmic electrical excitation is developed. The cardiac impulse arising from the sinus node is transmitted to the two atrial chambers (or atria) at the right and left sides of the heart. In response to excitation from the SA node, the atria contract, pumping blood from those chambers into the ventricles through the atrioventricular (AV) node, and via a conduction system comprising the bundle of His, or common bundle, the right and left bundle branches, and the Purkinje fibers. The transmitted impulse causes the ventricles to contract with the right ventricle pumping unoxygenated blood through the pulmonary artery to the lungs. The blood oxygenated by the lungs is carried via the pulmonary veins to the left atrium. The left ventricle then pumps oxygenated (arterial) blood through the aorta and the lesser arteries throughout the body.

The above action is repeated in a rhythmic cardiac cycle in which the atrial and ventricular chambers alternately contract and pump, and then relax and fill. One-way valves, between the atrial and ventricular chambers on the right and left sides of the heart, and at the exits of the right and left ventricles, prevent backflow of the blood as it moves through the heart and the circulatory system. This sinus node is spontaneously rhythmic, and the cardiac rhythm it generates is termed sinus rhythm. This capacity to produce spontaneous cardiac impulses is called rhythmicity. Some other cardiac tissue possess rhythmicity and hence constitute secondary natural pacemakers, but the sinus node is the primary natural pacemaker because it spontaneously generates electrical pulses at a faster rate. The secondary pacemakers tend to be inhibited by the more rapid rate at which impulses are generated by the sinus node.

Disruption of the natural pacemaking and propagation system as a result of aging or disease is commonly treated by artificial cardiac pacing, by which rhythmic electrical discharges are applied to the heart at a desired rate from an artificial pacemaker. A pacemaker is a medical device which delivers electrical pulses to an electrode that is implanted adjacent to or in the patient's heart to stimulate the heart so that it will contract and beat at a desired rate. If the body's natural pacemaker performs correctly, blood is oxygenated in the lungs and efficiently pumped by the heart to the body's oxygen-demanding tissues. However, when the body's natural pacemaker malfunctions, an implantable pacemaker often is required to properly stimulate the heart.

Implantable pacemakers are typically designed to operate using various different response methodologies, such as, for example, nonsynchronous or asynchronous (fixed rate), inhibited (stimulus generated in the absence of a specified cardiac activity), or triggered (stimulus delivered in response to a specific hemodynamic parameter). Generally, inhibited and triggered pacemakers may be grouped as "demand"-type pacemakers, in which a pacing pulse is only generated when demanded by the heart. To determine when pacing is required by the pacemaker, demand pacemakers may sense various conditions such as heart rate, physical exertion, temperature, and the like. Moreover, pacemaker implementations range from the simple fixed rate, single chamber device that provides pacing with no sensing function, to highly complex models that provide fully-automatic dual chamber pacing and sensing functions. For example, such multiple chamber pacemakers are described in U.S. Pat. No. 4,928,688 to Mower entitled "Method and Apparatus for Treating Hemodynamic Dysfunction," issued May 29, 1990; U.S. Pat. No. 5,792,203 to Schroeppel entitled "Universal Programmable Cardiac Stimulation Device," issued Aug. 11, 1998; U.S. Pat. No. 5,893,882 to Peterson et al. entitled "Method and Apparatus for Diagnosis and Treatment of Arrhythmias," issued Apr. 13, 1999; and U.S. Pat. No. 6,081,748 to Struble et al. entitled "Multiple Channel, Sequential Cardiac Pacing Systems," issued Jun. 27, 2000.

For example, a DDD pacer paces either chamber (atrium or ventricle) and senses in either chamber. Thus, a pacer in DDD mode, may pace the ventricle in response to electrical activity sensed in the atrium. Further, for example, a pacer operating in VVI mode, paces and senses in the ventricle, but its pacing is inhibited by spontaneous and electrical activity of the ventricle (i.e., intrinsic ventricular activity or events, wherein the ventricle paces itself naturally).

As such, it may be desired to sense in one cardiac chamber (e.g., detect electrical activity represented of contraction of a chamber and referred to as a "sensed event") and, in response, pace (referred to as a "paced event") in the same or different chamber. It also may be desired to pace at two electrode locations following a sensed event at one of the pacing electrodes or at a different electrode. For example, patients are often treated with pacemakers that include an electrode in each of the two atrial chambers and a third electrode in the right ventricle. Both atrial chambers usually are paced following a sensed event in either chamber.

Further, bi-ventricular pacing devices are also used for treatment of patients. For example, in such a bi-ventricular pacing apparatus, multiple implantable leads having electrodes associated with a part thereof are implanted to the respective chambers of a patient's heart and coupled to respective circuitry for forming multiple channels for pacing and sensing, e.g., left ventricular channel, right atrial channel, etc. Such an exemplary implantable, four-channel cardiac pacemaker is described in U.S. Pat. No. 6,070,101 to Struble et al. entitled "Multiple Channel, Sequential Cardiac Pacing Systems," issued May 30, 2000. For example, the distal end of a right atrial lead is attached to the right atrial wall and a right ventricular lead is passed through a vein into the right atrial chamber of the heart and into the right ventricle where its distal electrodes are fixed. Another lead is passed through a vein into the right atrial chamber of the heart, into the coronary sinus (CS), and then inferiorly into the great vein to extend a distal pair of left ventricular pace/sense electrodes alongside the left ventricular chamber and leave a proximal pair of left atrial pace/sense electrodes adjacent the left atrium. With such electrode placement, pacing and sensing can be performed in each chamber of the heart, enabling bi-ventricular pacing. For example, such bi-ventricular pacing may be performed following atrial sensed events or atrial paced events.

Typically in such types of pacing apparatus, if an intrinsic or pacing pulse occurs in one of the chambers, for example, the atrium, then this activity may be erroneously sensed in the other chambers due to cross-talk. In order to eliminate this type of error, in the past, pacemakers have been provided with blanking periods for blanking the sensor in one channel after a pacing pulse occurs in the other. This blanking period is usually referred to as the cross-channel blanking period. Following the blanking period, an alert period is normally designated during which the cardiac chamber of interest is monitored for intrinsic activity. If no such activity is sensed by the end of this alert, then a pacing pulse is applied to the chamber. However, one problem with such pacemakers and the use of blanking channels has been selecting the duration of the blanking period for a particular channel properly. If the blanking period is too short, a cross-channel artifact could be interpreted as an intrinsic activity and therefore pacing may be erroneously inhibited. On the other hand, if the blanking period is too long, intrinsic activity may be missed and the chamber may be paced when no such pacing is required. Either situation is undesirable physiologically.

Yet further, particularly in bi-ventricular pacing systems, e.g., systems which provide delivery of ventricular stimulus to both ventricular chambers following paced or sensed atrial events, a left ventricle lead is typically placed as described above, in a cardiac vein via the coronary sinus. Since the lead tip is in close proximity to the coronary sinus tractus, far-field coronary sinus/left atrial signals of significant amplitudes can potentially be sensed as ventricular activity and present inappropriate inhibition of bi-ventricular pacing. For example, in particular, when bipolar left ventricle leads are employed, the anode ring of the bipolar lead can be close to/or just within the coronary sinus system depending on tip-ring distance for the electrodes on the left ventricle lead. With the leads positioned in such a manner, atrial activity may be sensed using the left ventricle electrodes, taken as an intrinsic left ventricle event, and prevent or inhibit delivery of ventricular stimulus.

Further, for example, lead dislodgment may also lead to such mistaken sensing of ventricular events. For example, a left ventricular lead may be placed via the coronary sinus with a passive lead tip fixed in a cardiac vein. Leads are typically placed 1 to 4 centimeters within the vessels (or, generally, as far as possible). Either partial lead dislodgment (e.g., gradual pullback) or permanent lead dislodgment may result in an electrode location that is undesirable and conducive to over-sensing of left atrial activity. Therefore, once again, such over-sensing of atrial activity may lead to falsely sensed ventricular activity and the inhibition of the delivery of ventricular stimulus. As such, bi-ventricular stimulation may be intermittently or may be completely lost.

In many pacing apparatus, such as, for example, dual chamber pacing devices operating in DDD mode, ventricular safety pacing (VSP) is generally available and intended to prevent inappropriate inhibition of ventricular pacing by ensuring that an atrial paced event is followed by a ventricular paced event. When this VSP feature is on, ventricular sensing within a VSP window of typically 110 milliseconds following an atrial paced event causes ventricular pacing at the end of the VSP window (e.g., the 110 millisecond period).

For example, if the pacing apparatus is programmed with a paced AV interval (PAV=100 milliseconds) (i.e., the AV interval following an atrial paced event and defined as the time between the paced event and delivery of ventricular stimulus) that is less than the VSP window (e.g., 110 milliseconds), then the delivery of ventricular stimulus would occur at the end of the programmed PAV interval when ventricular sensing occurs during the VSP window.

In another example, if the pacing apparatus is programmed with a PAV interval (PAV=150 milliseconds) that is greater than the VSP window (VSP=110 milliseconds), then when ventricular sensing occurs during the VSP window, the delivery of ventricular stimulus would occur at the end of the VSP interval, and not at the time out of the PAV interval.

Further, with such conventional VSP, if no ventricular events are sensed during the VSP window and the PAV is greater in length than the VSP window, if a ventricular event is sensed during the PAV but after the VSP window, delivery of ventricular stimulus would be inhibited due to the sensed intrinsic ventricular event. This VSP feature is designed to ensure ventricular output in the event of noise sensing on the ventricular lead (e.g., cross-talk) within the VSP window or 110 milliseconds after an atrial paced event and outside the programmed ventricular blanking period.

Another example of a pacemaker having safety pacing is described in U.S. Pat. No. 5,782,881 to Lu et al., issued Jul. 21, 1998 and entitled "Pacemaker With Safety Pacing." As described therein, a monitoring window is defined during an AV delay during which signals sensed in a ventricular channel are monitored. If an abnormal signal is sensed during this window, certain features of the signal are analyzed to determine if its origin is intrinsic or due to cross-channel activity or noise. Cross-channel activity is ignored. If intrinsic cardiac activity is identified, then no pacing pulse or ventricular stimulation is applied. If no decision can be made as to the source of the cardiac activity, then delivery of stimulus is performed and ventricular pacing is not inhibited by the sensed activity.

The above-described VSP features may be inadequate in many circumstances. For example, conventional VSP features typically only occur when programmed on, and only following a paced atrial event. In other words, a VSP window is only utilized following delivery of pacing stimulus in the atrium and thus during a PAV interval. Such VSP features do not occur following atrial sensing or an atrial sensed event, where a timed sensed AV interval (SAV) is initiated.

Further, for example, in standard DDD pacemakers, when VSP is used, delivery of ventricular stimulus normally occurs following the expiration of the VSP window of 110 milliseconds, or at the termination of a PAV interval, whichever is less as previously described above. If the optimum PAV is programmed greater than 110 milliseconds (i.e., the PAV interval is longer than the VSP window), then normal delivery of stimulus at the termination of the 110 millisecond VSP window occurs too soon and not at termination of an optimum programmed PAV. In other words, such stimulus delivery at the termination of the VSP window will foreclose control of the heart by any intrinsic activity that may occur between the end of the VSP window and the termination of the PAV interval. As such, the optimized and programmed AV timing may be lost and competition to ventricular filling may occur.

Generally, optimized and programmed PAV intervals are significantly longer (e.g., 30–50 milliseconds) than SAV intervals. Fifty (50) milliseconds is generally required for slower conduction patients, for example, heart failure (HF) patients with conduction delays. For example, anticipated ranges for optimized SAV/PAV intervals in many patients may be, for example, SAV 80–130 milliseconds/PAV 130–180 milliseconds. Therefore, the problems associated with an optimum PAV programmed at a length greater than 110 milliseconds are readily apparent.

Yet further, as VSP does not typically occur following atrial sensing as described above, then any inappropriate over-sensing of intrinsic coronary sinus/left atrial signals during an SAV interval will result in the mistaken belief that a ventricular event has occurred and ventricular stimulation therapy is inhibited. This is particularly undesirable in atrial bi-ventricular pacing which is typically intended for heart failure patients with left bundle branch block (LBBB) and/or intraventricular conduction delay (IVCD) and intact sinus rhythm (SR). The expected majority of the therapy to be delivered in such patients is generally associated with sensed atrial events and operating with an SAV interval as opposed to paced atrial events operating with a PAV interval. As therapy operation with a PAV following a paced atrial event occurs only in the minority of such patients, use of standard or conventional VSP features for atrial bi-ventricular pacing that result only after atrial paced events operating with a PAV interval is limited.

Table I below lists U.S. patents relating to multiple chamber pacing devices and devices and methods having VSP features.

TABLE I

| U.S. Pat. No. | Inventor | Issue Date |
| --- | --- | --- |
| 4,928,688 | Mower | May 29, 1990 |
| 4,932,406 | Berkovits | Jun. 12, 1990 |
| 4,944,298 | Sholder | Jul. 31, 1990 |
| 5,144,949 | Olson | Sep. 8, 1992 |
| 5,292,340 | Crosby et al. | Mar. 8, 1994 |
| 5,318,594 | Limousine et al. | Jun. 7, 1994 |
| 5,782,881 | Lu et al. | Jul. 21, 1998 |
| 5,792,203 | Schroeppel | Aug. 11, 1998 |
| 5,893,882 | Peterson et al. | Apr. 13, 1999 |
| 5,902,324 | Thompson et al. | May 11, 1999 |
| 6,070,101 | Struble et al. | May 30, 2000 |
| 6,081,748 | Struble et al. | Jun. 27, 2000 |

All references listed in Table I, and elsewhere herein, are incorporated by reference in their respective entireties. As those of ordinary skill in the art will appreciate readily upon reading the Summary of the Invention, Detailed Description of the Embodiments, and claims set forth below, at least some of the devices and methods disclosed in the references of Table I and elsewhere herein may be modified advantageously by using the teachings of the present invention. However, the listing of any such references in Table I, or elsewhere herein, is by no means an indication that such references are prior art to the present invention.

SUMMARY OF THE INVENTION

The present invention has certain objects. That is, various embodiments of the present invention provide solutions to one or more problems existing in the prior art with respect to implantable medical device pacing techniques and, in particular, current ventricular safety pacing (VSP) techniques. One of such problems is that the current pacing apparatus generally apply VSP following only paced atrial events. Further, for example, pacing at the termination of the VSP window using current techniques may also not be adequate, e.g., when the PAV interval is longer than the VSP window. Yet further, for example, other problems involve the general inhibition of bi-ventricular stimulation therapy due to inappropriate over-sensing of intrinsic coronary sinus/lower left atrial signals during AV intervals and inhibition of ventricular stimulus due at least in part to lead dislodgment and inappropriate sensing thereafter.

In comparison to known VSP techniques, various embodiments of the present invention may provide one or more of the following advantages. For example, VSP according to the present invention always ensures pacing therapy at the optimized programmed SAV and PAV intervals, i.e., SAV and PAV delays. Further, such committed delivery of ventricular stimulation therapy at the optimized SAV and PAV intervals is ensured even with the occurrence of inappropriate coronary sinus/left atrial far-field sensing, even with the occurrence of post-atrial paced ringing, even with the occurrence and sensing of coronary sinus/left atrial intrinsic signals; etc. This ensured ventricular pacing therapy at the optimized programmed SAV and PAV intervals is provided by not only establishing committed VSP following a paced atrial event, but also following a sensed atrial event.

Some embodiments of the method of the present invention include one or more of the following features: providing a sensed AV delay following an atrial sensed event with the sensed AV delay being a predetermined time period initiated thereby; defining a VSP window during at least an initial portion of a sensed AV delay with the sensed AV delay further including a remainder portion thereof subsequent to the initial portion; sensing ventricular events during the sensed AV delay; delivering ventricular stimulus upon expiration of the sensed AV delay if no ventricular events are sensed during the VSP window defined during the initial portion of the sensed AV delay and the reminder portion thereof; inhibiting the delivery of ventricular stimulus upon expiration of a sensed AV delay if no ventricular events are sensed during the VSP window but a ventricular event is sensed during a remainder portion of the sensed AV delay; committing to the delivery of a ventricular stimulus upon expiration of a sensed AV delay if a ventricular event is sensed during a VSP window; defining a VSP window during an initial portion of a sensed AV delay that is 110 milliseconds; and defining a sensed AV delay that is equal to or greater than a VSP window.

Other embodiments of the method of the present invention include one or more of the following features: providing a paced AV delay following an atrial paced event with the paced AV delay being a predetermined time period initiated thereby; defining a VSP window during at least an initial portion of the paced AV delay with the paced AV delay further comprising a remainder portion thereof subsequent to the initial portion; sensing ventricular events during the paced AV delay; delivering ventricular stimulus upon expiration of the paced AV delay if no ventricular events are sensed during a VSP window defined during an initial portion of a paced AV delay and the remainder portion thereof; inhibiting the delivery of ventricular stimulus upon expiration of the paced AV delay if a ventricular event is not sensed during the VSP window but a ventricular event is sensed during the remainder portion of the paced AV delay; committing to delivery of ventricular stimulus upon expiration of the paced AV delay if a ventricular event is sensed during the VSP window; defining a paced AV delay and a sensed AV delay that are both greater than a VSP window; defining a paced AV delay that is greater than the sensed AV delay; delivering bi-ventricular stimulus; and providing an AV delay initiated by occurrence of either an atrial sensed event or an atrial paced event with the AV delay being a programmed time period whose length is varied depending upon whether the AV delay is initiated by the occurrence of an atrial sensed event or is initiated by the occurrence of an atrial paced event.

Further, some embodiments of an apparatus according to the present invention include one or more of the following features: a dual chamber pacing apparatus; atrial pacing and sensing circuitry to generate atrial pacing pulses and sense atrial events; ventricular pacing and sensing circuitry to generate ventricular pacing pulses and sense ventricular events; control circuitry operable to provide a sensed AV delay following an atrial sensed event detected using the atrial sense circuitry with the sensed AV delay being a predetermined time period initiated by the atrial sensed event; control circuitry operable to define a VSP window during at least an initial portion of the sensed AV delay with the sensed AV delay further including a remainder portion thereof subsequent to the initial portion; control circuitry operable to detect ventricular events using the ventricular sensing circuitry during a sensed AV delay; control circuitry operable to control delivery of ventricular stimulus using the ventricular pacing circuitry upon expiration of a sensed AV delay such that if no ventricular events are detected during the VSP window defined during the initial portion of the sensed AV delay and the remainder portion thereof then ventricular stimulus is deliver at the expiration of the sensed AV delay; control circuitry operable to control delivery of ventricular stimulus using the ventricular pacing circuitry upon expiration of a sensed AV delay such that if a ventricular event is not detected during the VSP window but a ventricular event is detected during the remainder portion of the sensed AV delay then delivery of ventricular stimulus upon expiration of the sensed AV delay is inhibited; and control circuitry operable to control delivery of ventricular stimulus using the ventricular pacing circuitry upon expiration of a sensed AV delay such that if a ventricular event is sensed by the ventricular sensing circuitry during the VSP window then the ventricular pacing circuitry is committed to delivery of ventricular stimulus upon expiration of the sensed AV delay.

Yet further, other embodiments of the apparatus may include one or more of the following features: control circuitry operable to provide a paced AV delay following an atrial paced event with the paced AV delay being a predetermined time period initiated by the occurrence of an atrial paced event resulting from the generation of atrial pacing pulses by the atrial pacing circuitry; control circuitry operable to define a VSP window during at least an initial portion of a paced AV delay with the paced AV delay further including a remainder portion thereof subsequent to an initial portion; control circuitry operable to control delivery of ventricular stimulus using the ventricular pacing circuitry upon expiration of a paced AV delay such that if no ventricular events are detected during the VSP window defined during the initial portion of the paced AV delay and the remainder portion thereof then ventricular stimulus is deliver at the expiration of the paced AV delay; control circuitry operable to control delivery of ventricular stimulus using the ventricular pacing circuitry upon expiration of a paced AV delay such that if a ventricular event is not detected during the VSP window but a ventricular event is detected during the remainder portion of the paced AV delay then delivery of ventricular stimulus upon expiration of the paced AV delay is inhibited; control circuitry operable to control delivery of ventricular stimulus using the ventricular pacing circuitry upon expiration of a paced AV delay such that if a ventricular event is sensed by the ventricular sensing circuitry during the VSP window then the ventricular pacing circuitry is committed to delivery of ventricular stimulus upon expiration of the paced AV delay; bi-ventricular pacing and sensing circuitry to generate bi-ventricular pacing pulses and sense ventricular events; and control circuitry operable to provide an AV delay initiated by occurrence of either an atrial sensed event detected by atrial sensing circuitry or an atrial paced event associated with the generation of atrial pacing pulses using atrial pacing circuitry with the AV delay being a programmed time period whose length is varied depending upon whether the AV delay is initiated by the occurrence of an atrial sensed event or is initiated by the occurrence of an atrial paced event.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

BRIEF DESCRIPTION OF THE DRAWINGS

The present invention will be further described with reference to the drawings, wherein.

DETAILED DESCRIPTION OF THE EMBODIMENTS

Figure 1:
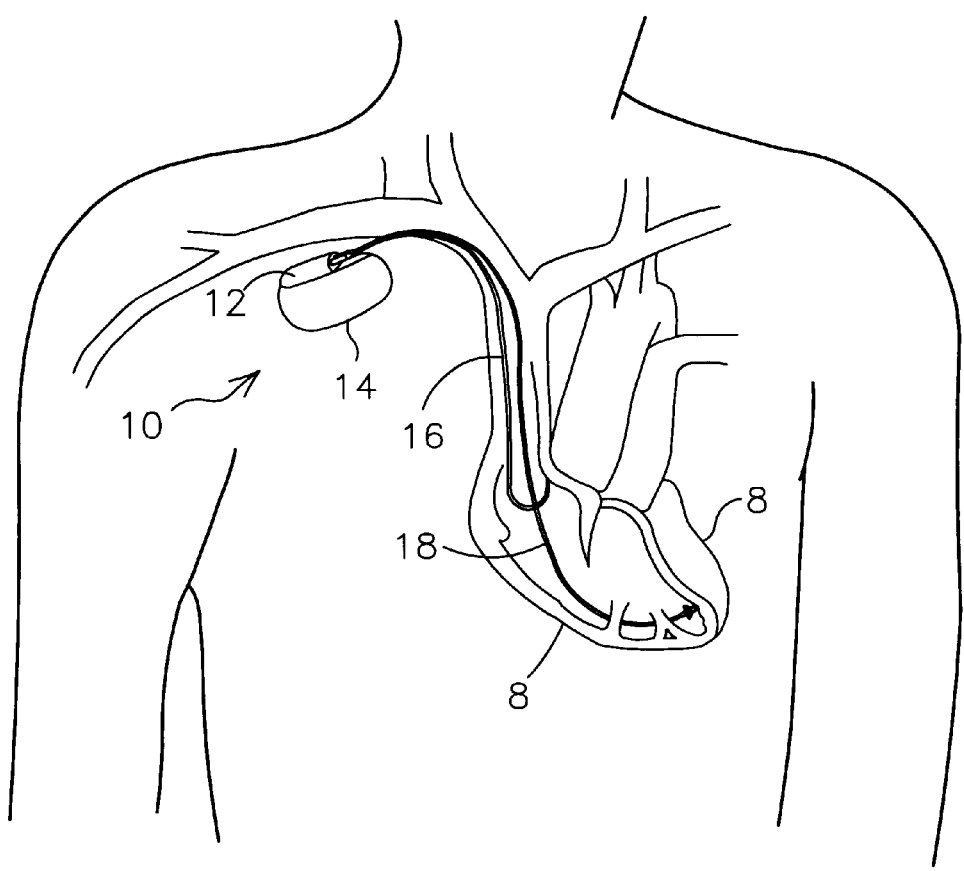
FIG. 1 is an implantable medical device (IMD) in accordance with one embodiment of the present invention, wherein the IMD is implanted within a body of a patient.

FIG. 1 is a simplified view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18, sense electrical signals attendant to the depolarization and re-polarization of the heart 8, and further provide pacing pulses for causing depolarization of cardiac tissue in the vicinity of the distal ends thereof. Leads 16 and 18 may have, for example, unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson.

Figure 2:
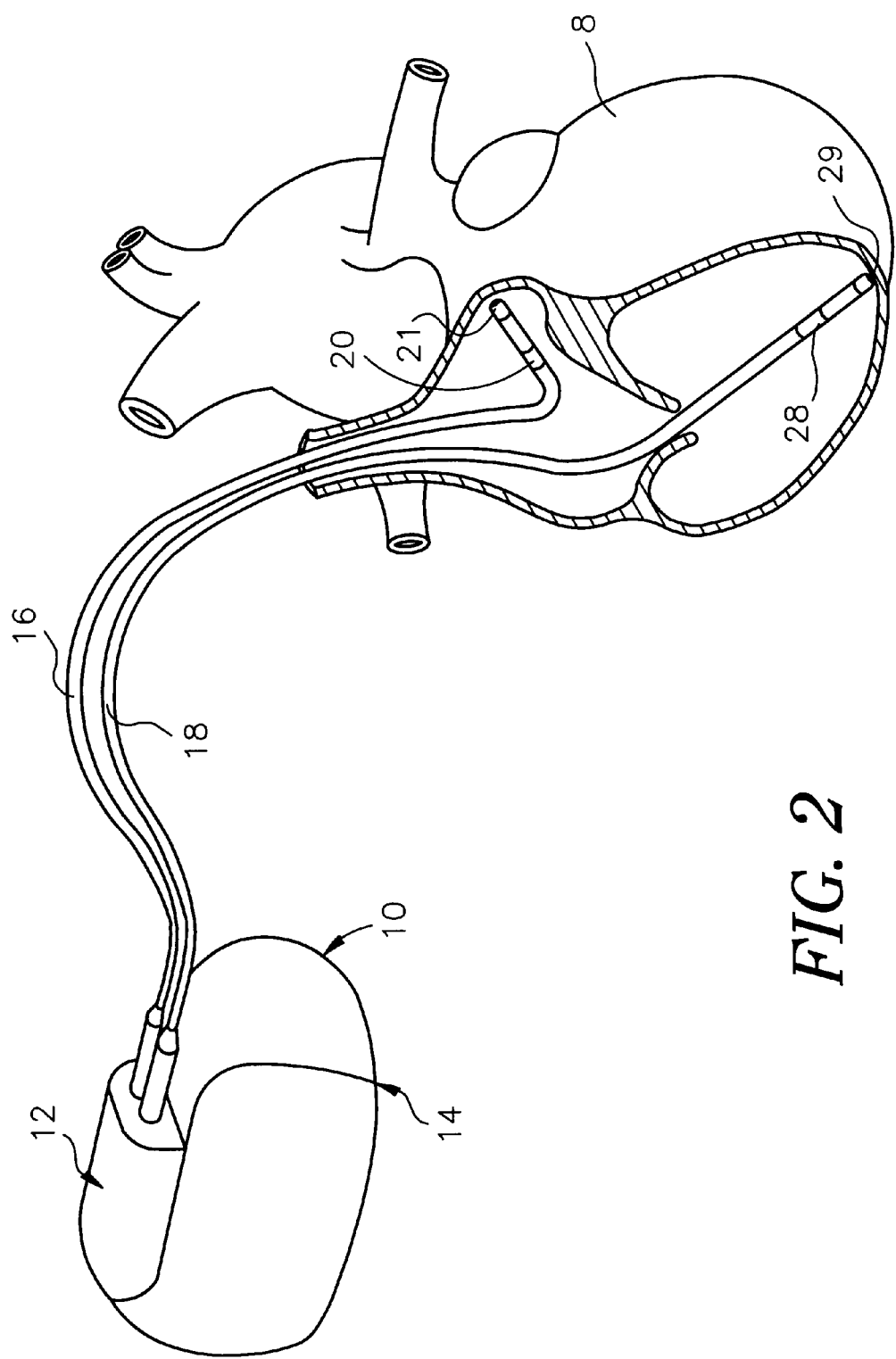
FIG. 2 is an enlarged view of the IMD of FIG. 1 diagrammatically illustrating coupling with the patient's heart in accordance with one embodiment of the invention.

FIG. 2 shows connector module 12 and hermetically sealed enclosure 14 of IMD 10 located near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
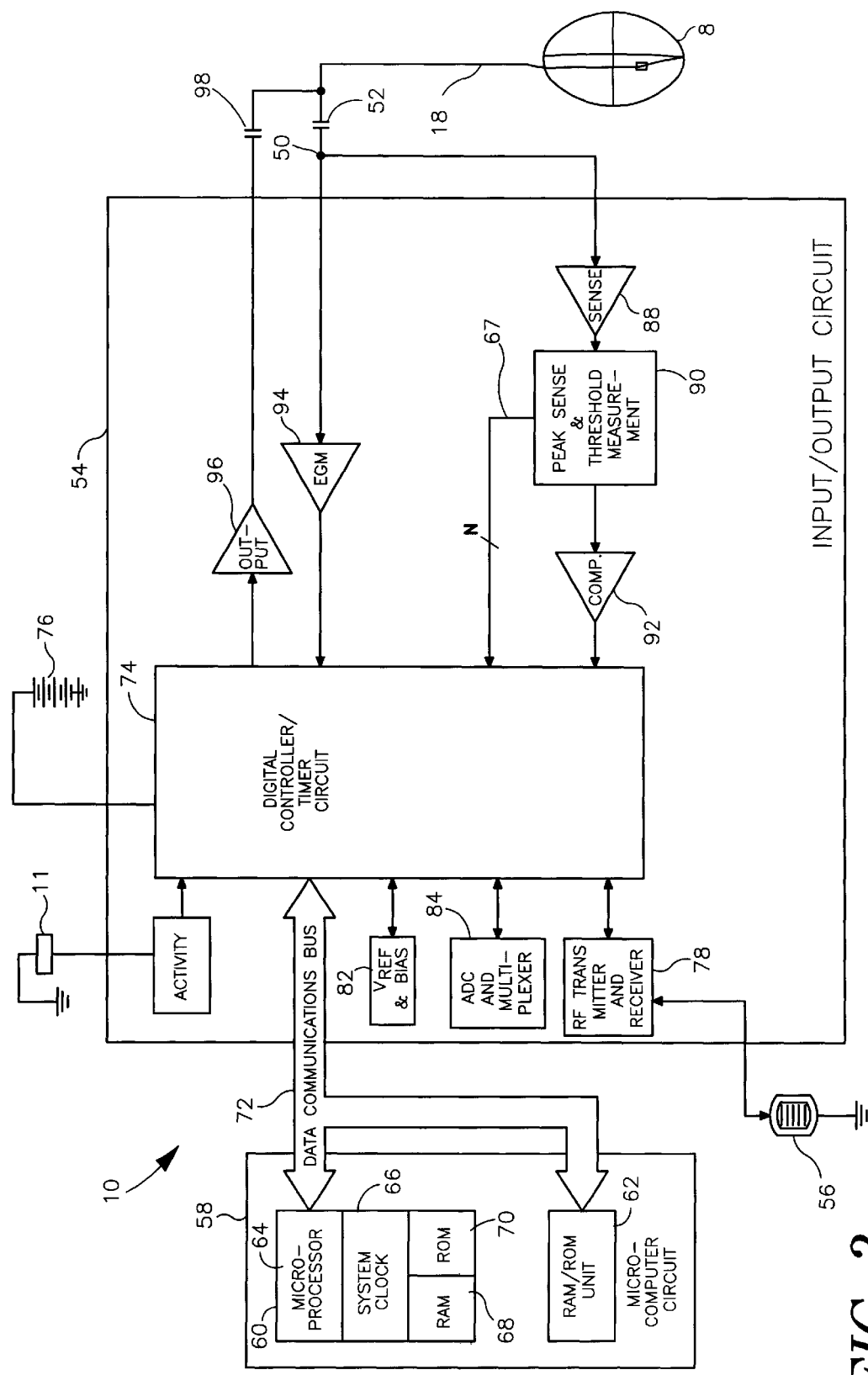
FIG. 3 is a functional block diagram of an IMD in accordance with one embodiment of the present invention.

FIG. 3 is a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,354,319 to Wyborny et al. The programming methodology disclosed in Wyborny et al.'s '319 patent is identified herein for illustrative purposes only. Any of a number of suitable programming and telemetry methodologies known in the art may be employed so long as the desired information is transmitted to and from IMD 10.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,556,063 issued to Thompson et al., or to that disclosed in the above-referenced '319 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

$V_{REF}$ and Bias circuit 82 (see FIG. 3) most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54 and for particular employing certain functionality such as ventricular safety pacing in accordance with the present invention.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al. Output pulse generator 96 provides pacing stimuli to patient's heart 8 through coupling capacitor 98, for example, in response to a pacing trigger signal provided by digital controller/timer circuit 74 each time the escape interval times out, in response to an externally transmitted pacing command or in response to other stored commands as is well known in the pacing art. By way of example, output amplifier 96 may correspond generally to an output amplifier disclosed in U.S. Pat. No. 4,476,868 to Thompson.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some embodiments of the present invention, IMD 10 may operate in various non-rate-responsive modes, including, but not limited to, DDD, DDI, VV, VOO and VVT modes. In other embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate-responsive modes. Moreover, in various embodiments of the present invention, IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to dual-sensor pacemakers, and is not limited to IMD's comprising activity or pressure sensors only. Further, the present invention is not limited in scope to dual-chamber pacemakers, dual-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of dual-, triple- or quadruple-chamber pacemakers or other types of IMD's. See, for example, U.S. Pat. No. 5,800,465 to Thompson et al.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker, Jr. et al.

Figure 4:
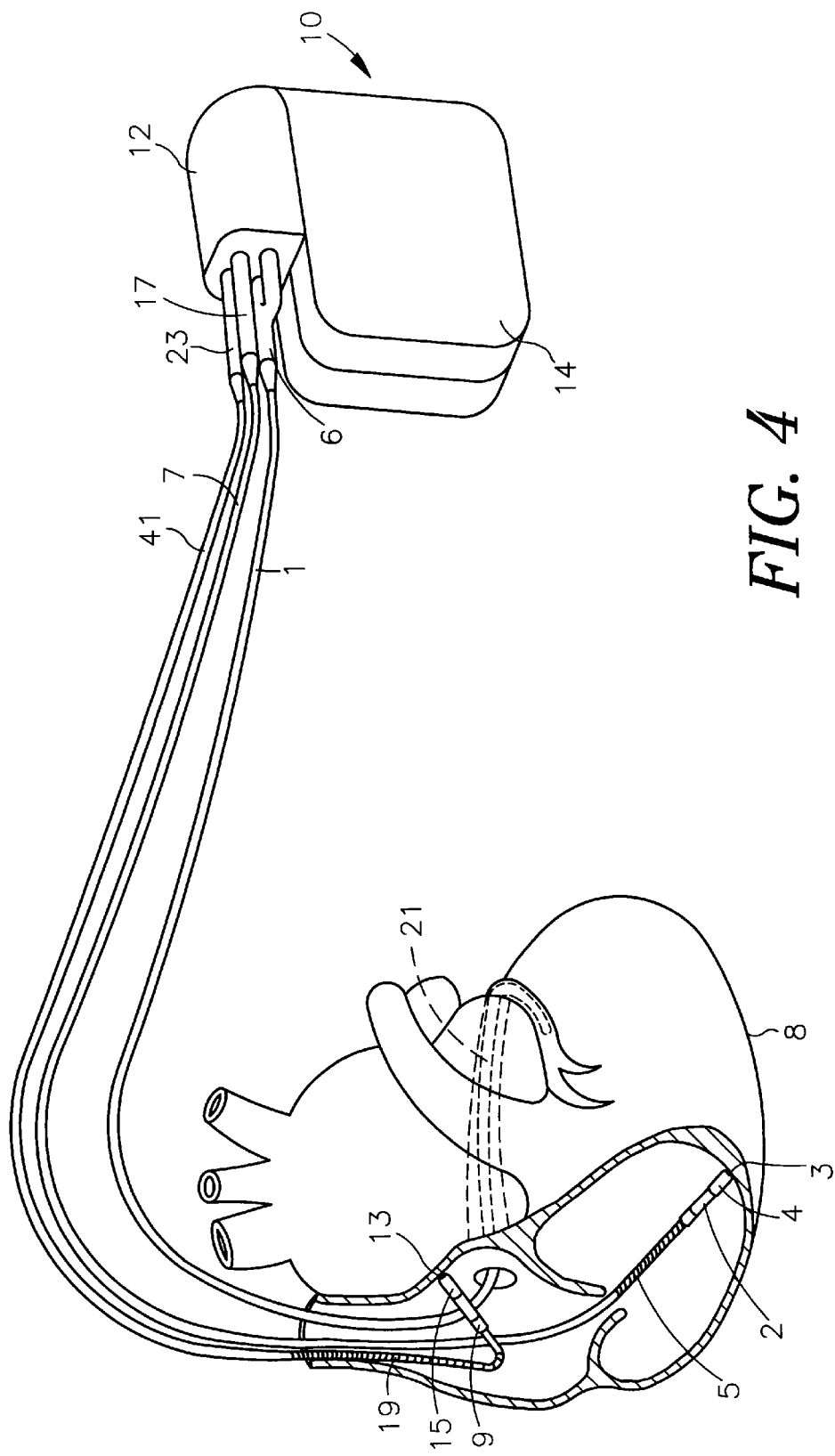
FIG. 4 is an IMD in accordance with another embodiment of the invention, wherein the IMD is an implantable pacemaker/cardioverter/defibrillator (PCD)
Figure 5:
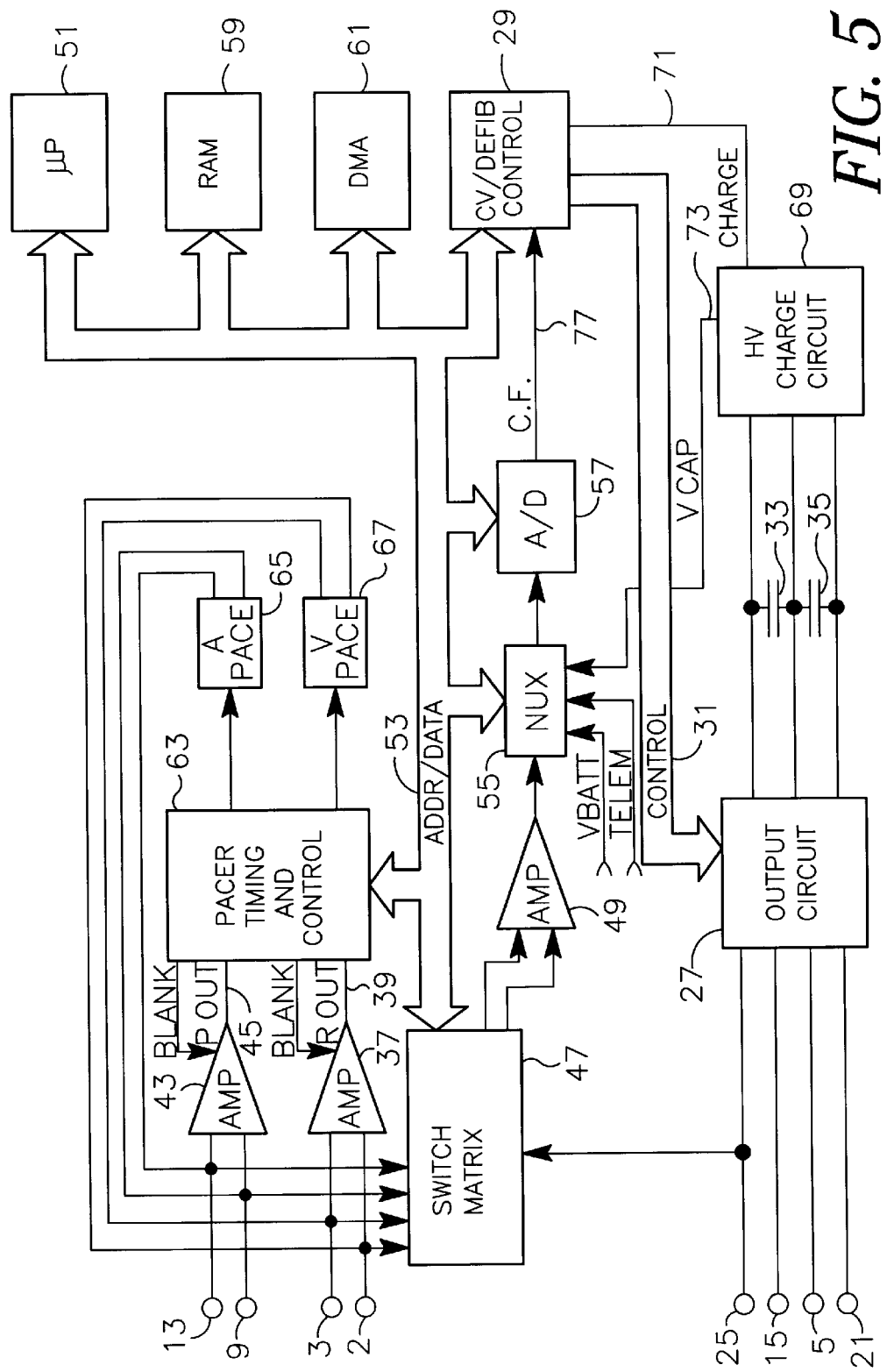
FIG. 5 is a functional block diagram of the IMD of FIG. 4.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

The implantable PCD is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other than those shown in FIG. 4 may be practiced in conjunction with the present invention, such as those shown in U.S. Pat. No. 5,690,686 to Min et al.

FIG. 5 is a functional schematic diagram of one embodiment of an implantable POD of the present invention. This diagram should be taken as exemplary of the type of device in which various embodiments of the present invention may be embodied, and not as limiting, as it is believed that the invention may be practiced in a wide variety of device implementations which provided pacing therapies.

The PCD is provided with an electrode system. If the electrode configuration of FIG. 4 is employed, the electrode configuration correspondence may be as follows. Electrode 25 in FIG. 5 includes the uninsulated portion of the housing of the POD. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, to Keimel et al.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selection may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known in the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann et al., U.S. Pat. No. 4,880,005 issued to Pless et al. and U.S. Pat. No. 4,830,006 issued to Haluska et al. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May-June, 1984, pp. 541–547.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al. and U.S. Pat. No. 4,587,970, issued to Holley et al., may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and, in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy, microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al. However, any known cardioversion or defibrillation pulse control circuitry is believed to be usable in conjunction with various embodiments of the present invention. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. Examples of output circuitry for delivery of biphasic pulse regimens to multiple electrode systems may be found in U.S. Pat. No. 4,953,551 to Mehra et al. and in U.S. Pat. No. 4,727,877 to Kallock.

An example of circuitry which may be used to control delivery of monophasic pulses is disclosed in U.S. Pat. No. 5,163,427 to Keimel. Output control circuitry similar to that disclosed in the above-cited patent issued to Mehra et al. or U.S. Pat. No. 4,800,883 to Winstrom, may also be used in conjunction with various embodiments of the present invention to deliver biphasic pulses.

Figure 6:
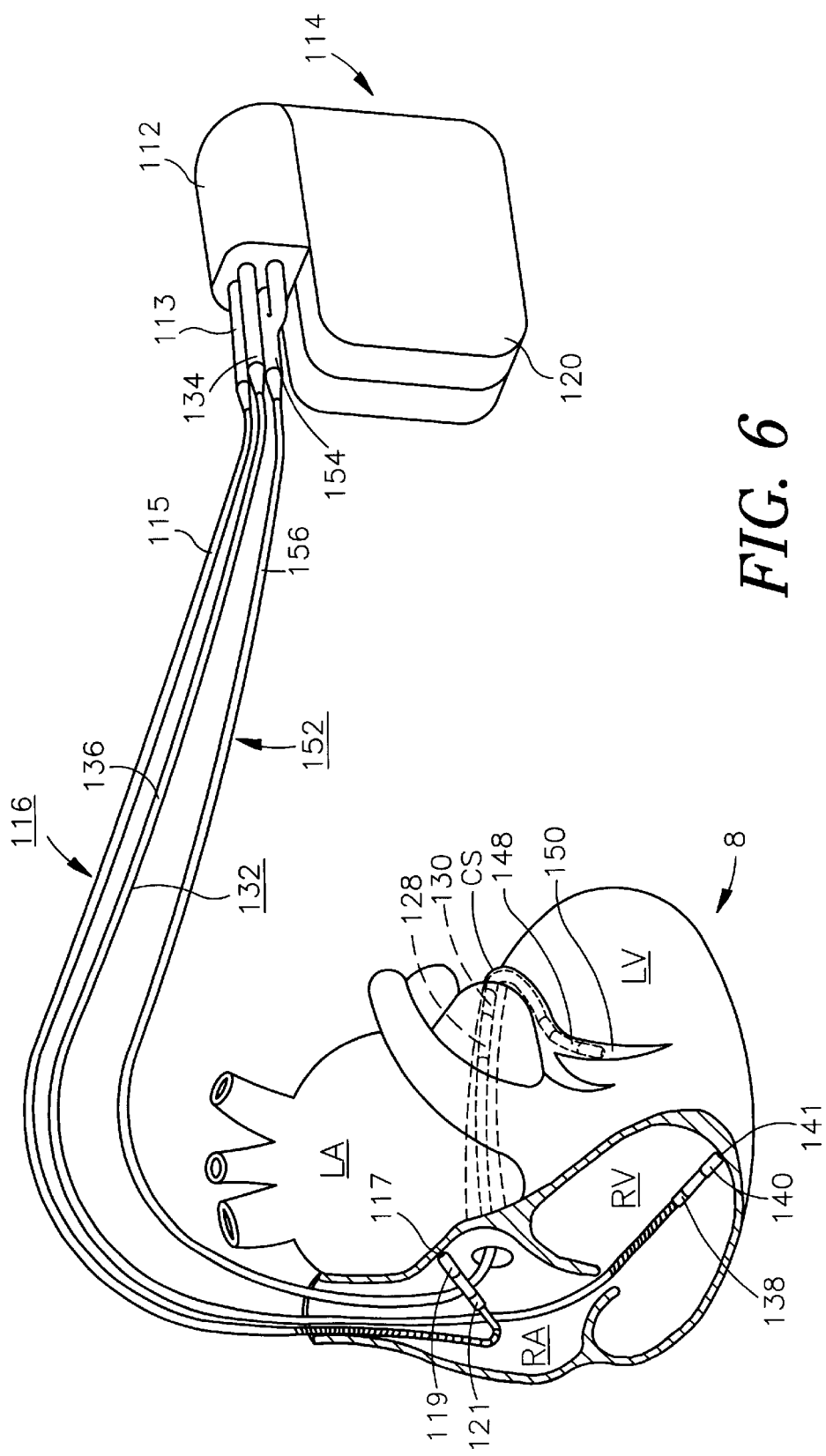
FIG. 6 is a diagram of an IMD illustrating a multiple channel bi-atrial and/or bi-ventricular pacing system coupled with a patient's heart in accordance with another embodiment of the present invention.

FIG. 6 is a schematic representation of an implantable medical device (IMD) 114 that includes a four-channel cardiac pacemaker such as that described in U.S. Pat. No. 6,070,101 to Struble et al. entitled "Multiple Channel, Sequential, Cardiac Pacing Systems," issued May 30, 2000. The inline connector 113 of a right atrial lead 116 is fitted into a bipolar bore of IMD connector block 112 and is coupled to a pair of electrically insulated conductors within lead body 115 that are connected with distal tip right atrial pace-sense electrode 119 and proximal ring right atrial pace-sense electrode 121. The distal end of the right atrial lead 116 is attached to the right atrial wall by a conventional attachment mechanism 117. Bipolar endocardial right ventricle lead 132 is passed through the vein into the right atrial chamber of the heart 8 and into the right ventricle where its distal ring and tip right ventricular pace-sense electrodes 138 and 140 are fixed in place in the apex by a conventional and distal attachment mechanism 141. The right ventricular lead 132 is formed with an inline connector 134 fitting into a bipolar bore of IMD connector block 112 that is coupled to a pair of electrically insulated conductors within lead body 136 and then connected with distal tip right ventricular pace-sense electrode 140 and proximal ring right ventricular pace-sense electrode 138.

In this particular illustrative embodiment, although other types of leads may be used, a quadripolar, endocardial left ventricular coronary sinus (CS) lead 152 is passed through a vein into the right atrial chamber of the heart 8, into the CS, and then inferiorly in the great vein to extend to the distal pair of left ventricular CS pace-sense electrodes 148 and 150 alongside the left ventricular chamber and leave the proximal pair of left atrial CS pace-sense electrodes 128 and 130 adjacent the left atrial chamber. The left ventricular CS lead 152 is formed with a four-conductor lead body 156 coupled at the proximal end to a bifurcated inline connector 154 fitting into a pair of bipolar bores of IMD connector block 112. The four electrically insulated lead conductors in left ventricular CS lead body 156 are separately connected with one of the distal pair of left ventricular CS pace-sense electrodes 148 and 150 and the proximal pair of left atrial CS pace-sense electrodes 128 and 130.

The IMD 114 may comprise, for example, similar circuitry and connections as shown in FIG. 3 for each of the multiple leads to establish the multiple pacing/sensing channels provided for each respective pair of pace-sense electrodes associated with each chamber of the heart as shown in FIG. 6. For the sake of convenience, such circuitry is not described further. For example, channel circuitry for pacing/sensing the left atrial chamber is associated with pace-sense electrodes 28 and 30 adjacent the left atrium. One skilled in the art will recognize that each sensing/pacing channel may include a sense amplifier and pace output pulse generator coupled through the respective pacing/sensing lead. Although the pacing system shown in FIG. 6, shall not be described in detail for simplicity purposes, it will be recognized that multiple chambers may be paced/sensed via respective channels for such chambers. As such, for example, bi-atrial and/or bi-ventricular pacing may be performed as would be readily apparent to one skilled in the art.

With various embodiments of medical devices, e.g., implantable medical devices, described above, it will become apparent from the description below that the present invention may be applied to any ventricular pacing system, e.g., dual chamber pacing system. For example, the present invention may be applied to a three-chamber atrial-bi-ventricular pacing apparatus, a dual chamber pacing apparatus, a dual chamber defibrillator, etc. In other words, the present invention may be applied to any implantable medical device that provides pacing of at least one ventricle, whether such pacing is based on paced atrial events or sensed atrial events. For example, some devices that may be modified to include the ventricular safety pacing techniques according to the present invention may include, for example, the InSync, InSync-ICD, or InSync III three chamber atrial-bi-ventricular pacers; all VDD(R)/DDD(R) pacemakers including dual chamber right atrial/left ventricular pacers; Jewel DR DDD(R)-ICD; dual chamber (right atrial/left ventricular) defibrillators, and three chamber DDD(R)-ICD pacing devices available from Medtronic Inc.

Figure 7:
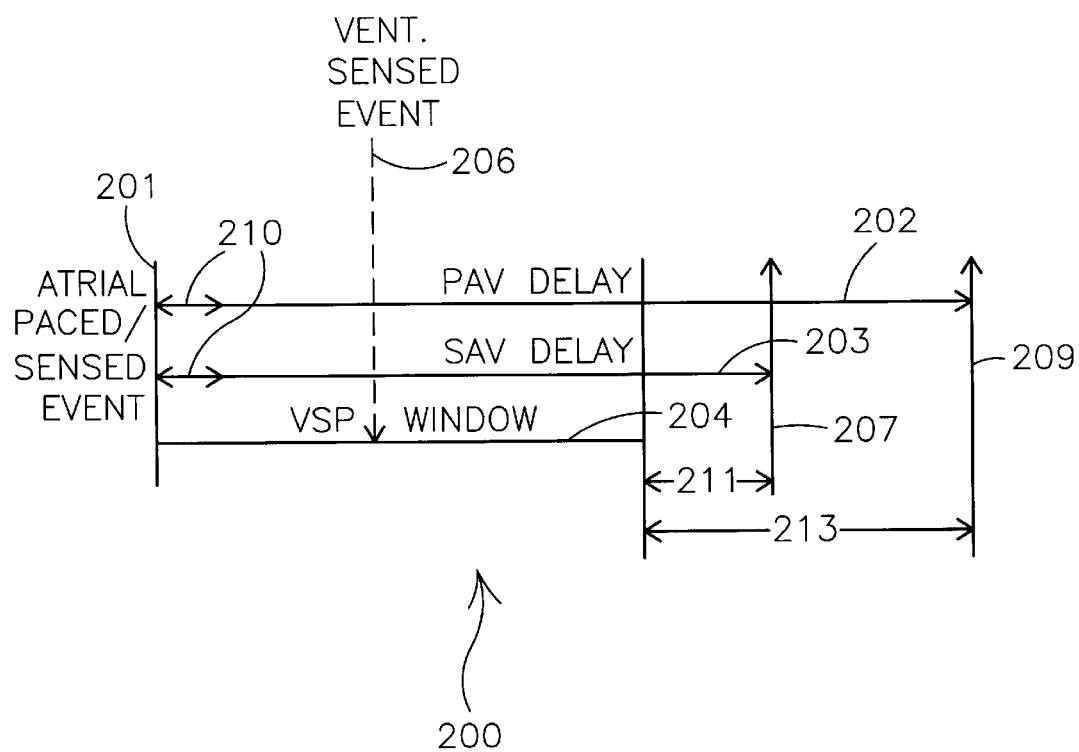
FIG. 7 is a timing diagram illustrating ventricular safety pacing according to the present invention.

Generally, FIG. 7 shows a timing diagram 200 that is illustrative of the ventricular safety pacing (VSP) features according to the present invention. Such features shall be described with respect to a pacing and sensing system operating in DDD mode. However, one skilled in the art will readily recognize that other modes and systems may utilize the present invention as described herein.

Delivery of ventricular pacing, e.g., bi-ventricular pacing, at optimized SAV and PAV delays is ensured according to the present invention without such pacing being inhibited by false ventricular sensing, e.g., sensing of cross-talk, post atrial pacing ringing, etc. Such ensured delivery of ventricular pacing is accomplished through use of a VSP window 204 as shown in timing diagram 200 of FIG. 7.

As shown in FIG. 7, following an atrial sensed or paced event 201, a ventricular blanking period 210 occurs. This blanking period is a very brief interval initiated by the atrial paced/sensed event 201 during which ventricular sensing cannot occur. Typically, an atrial stimulus disables ventricular sensing for a 25–35 millisecond period to prevent inadvertent sensing of the atrial stimulus by a ventricular channel, thereby preventing inappropriate inhibition of delivery of ventricular stimulus. If a blanking period 210 was not used, cross-talk between the atrial and ventricular channels might lead to the undesirable inhibition of the delivery of ventricular stimulus by the pacemaker.

The blanking period 210 falls within the AV interval, e.g., paced AV (PAV) interval 202 and/or sensed AV (SAV) interval 203. The AV interval is the interval between either an atrial sensed event or an atrial paced event 201 and delivery of a ventricular stimulus. For example, following an atrial paced event 201 is a PAV interval 202 extending from the atrial paced event 201 to delivery of a ventricular stimulus 209. Likewise, the SAV interval 203 is the interval between a sensed atrial event 201 and delivery of ventricular stimulus 207.

In general, the PAV interval 202 is a programmed time delay between the paced atrial event 201 and when delivery of ventricular stimulus 209 is to occur thereafter (if no intrinsic ventricular activity is sensed). Likewise, the SAV interval 203 is a programmed AV delay between a sensed atrial event 201 and when ventricular stimulus is delivered 207 thereafter (if no intrinsic ventricular activity is sensed). As such, as used hereinafter, the SAV delay and the PAV delay represent the programmed AV interval initiated by an atrial sensed or atrial paced event 201, respectively, and such terms "AV interval" and "AV delay" are used interchangeable herein.

A sensed atrial event or beat, i.e., a P-wave, will start a programmed SAV delay. For example, if such depolarization of the atrium is sensed, then a SAV timer is started. If the atrium is paced, such an atrial beat will start a programmed PAV delay. For example, a programmed PAV interval, e.g., a software interval, may be initiated. One will recognize that various hardware and software may be used to implement the various timing intervals of the present invention. For example, the circuitry shown in FIG. 3 may be used to implement the present invention, e.g., the processing circuitry and timing circuitry.

When VSP according to the present invention is turned on, programmed on, or, in other words, when this particular VSP feature is enabled, then a VSP window 204 is defined during at least an initial portion of a sensed AV delay 203 or a paced AV delay 202. The VSP window 204 is the time period, e.g., 0 to 110 milliseconds, of the AV interval, e.g., PAV delay or SAV delay, during which if sensed ventricular events or activity are detected, delivery of ventricular stimulus is committed upon the expiration of the PAV or SAV delay. In other words, the VSP window 204 is defined such that upon ventricular sensing during the VSP window 204, VSP pacing at the termination of the SAV delay or PAV delay occurs irrespective of any other signals sensed during the SAV delay or PAV delay.

Upon occurrence of an atrial paced event 201, a PAV delay 202 is initiated. VSP window 204 is defined during an initial portion of the PAV delay 202 with a remainder portion 213 subsequent to the initial portion occupied by VSP window 203. Likewise, upon occurrence of a sensed atrial event 201, VSP window 204 is defined during an initial portion of SAV delay 203 with a remainder portion 211 being subsequent to the initial portion occupied by VSP window 204.

Therefore, in other words, for example, the SAV programmed delay or interval 203 can be looked at as including an initial time period, e.g., 0–110 milliseconds, corresponding to the VSP window 204 and a remainder time period 211 before delivery of the ventricular stimulus 207 (assuming no intrinsic events are sensed in the remainder time period 211). For example, if the SAV delay 203 is programmed to 120 milliseconds, then the first 110 milliseconds may be the VSP window 204, and an additional remainder 10 milliseconds will be the remainder portion 211 that follows the VSP window 204 prior to termination of the SAV programmed delay 203.

Likewise, the PAV programmed delay or interval 202 can be looked at as including an initial time period, e.g., 0–110 milliseconds, corresponding to the VSP window 204 and a remainder time period 213 before delivery of the ventricular stimulus 209 (assuming no intrinsic events are sensed in the remainder time period 213). For example, if the PAV delay 202 is programmed to 150 milliseconds, then the first 110 milliseconds may be the VSP window 204, and an additional 40 milliseconds will be the remainder portion 213 that follows the VSP window 204 prior to termination of the PAV programmed delay 202.

Preferably, VSP window 204 is 110 milliseconds. Further, preferably, the SAV delay 203 is greater in length than the VSP window 204. Likewise, preferably, the PAV delay 202 is greater in length than the VSP window 204.

Generally, the PAV delay 202 as optimized and programmed is significantly longer than the SAV delay 203. For example, an anticipated range in most patients for optimized SAV/PAV delays is about SAV 80–130 milliseconds/PAV 130–180 milliseconds. For example, the difference between SAV delay and PAV delay is typically 30 milliseconds to 50 milliseconds. Further, for example, if the SAV delay is equal to 120 milliseconds, then the PAV delay is typically equal to about 150–170 milliseconds. The PAV delay is usually longer than SAV delay because there is a time period between delivery of pacing stimulus to the atrium and the onset (i.e., lag time) of the atrial depolarization (i.e., P-wave) which is absent when an atrial event is sensed. In sensed atrial events, the stimulus has already been delivered, and only the resulting P-wave depolarization signal is seen. This lag time is typically about 30–50 milliseconds. A lag time of about 50 milliseconds for SAV delay relative to PAV delay is generally necessary to accommodate for slower conduction in HF patients with conduction delays.

As shown in FIG. 7, preferably the VSP window 204 is defined at the same fixed interval for both a PAV delay 202 and an SAV delay 203. Further, as indicated above, the VSP window is preferably 110 milliseconds as, generally, any signal sensed on the ventricular channel within 110 milliseconds of any atrial event, cannot be a truly conducted intrinsic ventricular beat because such an intrinsic ventricular event would take significantly longer to occur. Therefore, this sensed signal during such a 110 millisecond interval must be a false signal. Such a signal sensed during this time period may be, for example, post atrial ringing, EMI, PVC, etc. As a pacemaker cannot discriminate whether it is a false or intrinsic ventricular signal, ventricular inhibition based on an early (0 to 110 millisecond) signal from any uncertain source must be prevented at all times.

Therefore, according to the present invention, if any ventricular sensing occurs at all in the VSP window 204, then a ventricular stimulus is always committed at the termination of the SAV or PAV delay, irrespective of any further sensing which might occur at a later time, e.g., in the remainder of the SAV or PAV. In other words, if a false signal, e.g., EMI, is sensed in the VSP window 204, then this same signal may be sensed in a later period. Such a later false sensing signal cannot be allowed to lead to ventricular pacing inhibition. With use of committed pacing following a sensed event in the VSP window 204 as described above, inhibition based on such a false signal is prevented.

The optimized or programmed PAV and SAV delays are set at lengths determined specifically on a patient-by-patient basis. Such values are set to provide optimized pacing delivery for such patients.

Figure 8:
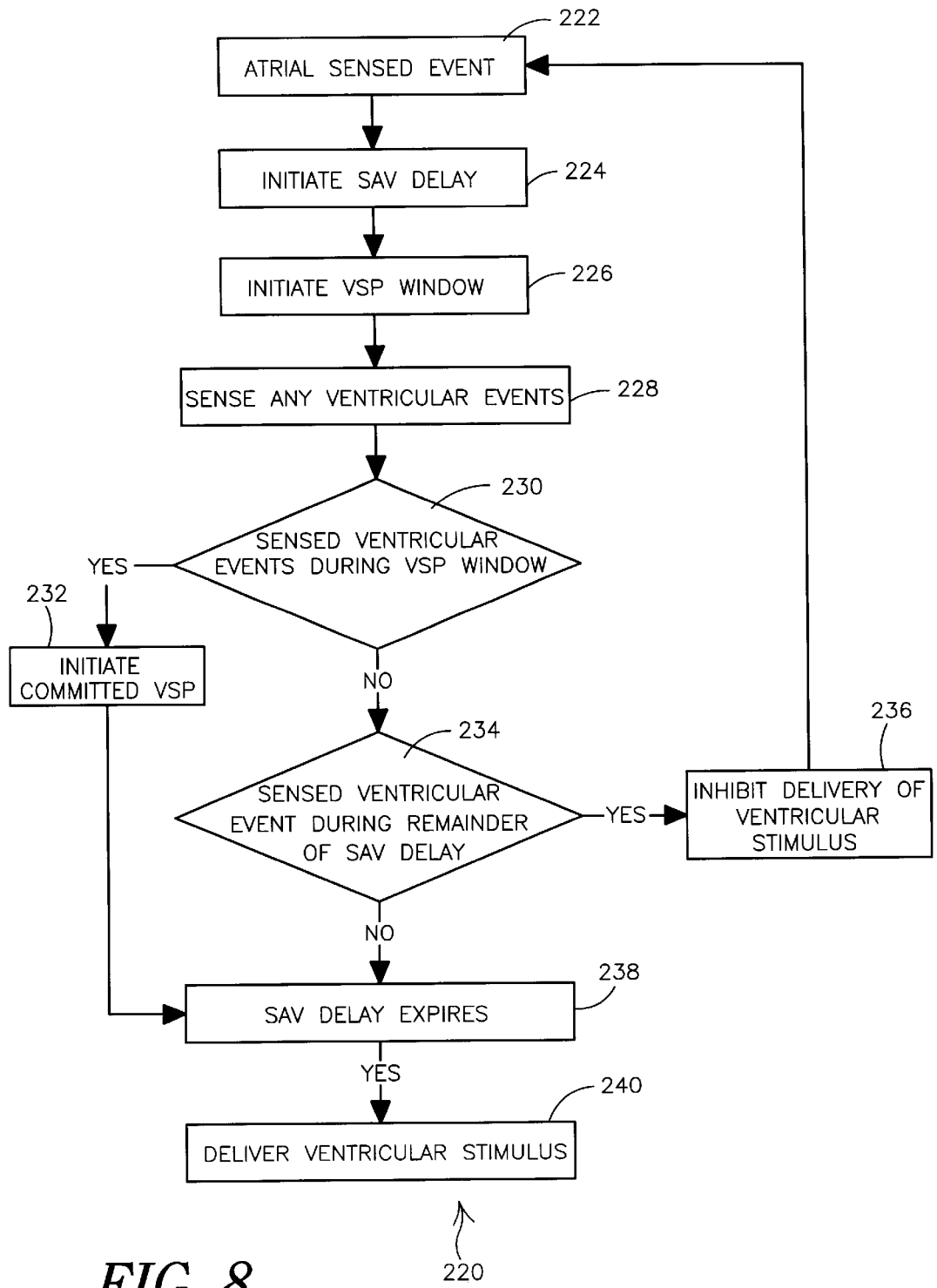
FIG. 8 is a flow diagram for use in describing ventricular pacing following an atrial sensed event according to the present invention.
Figure 9:
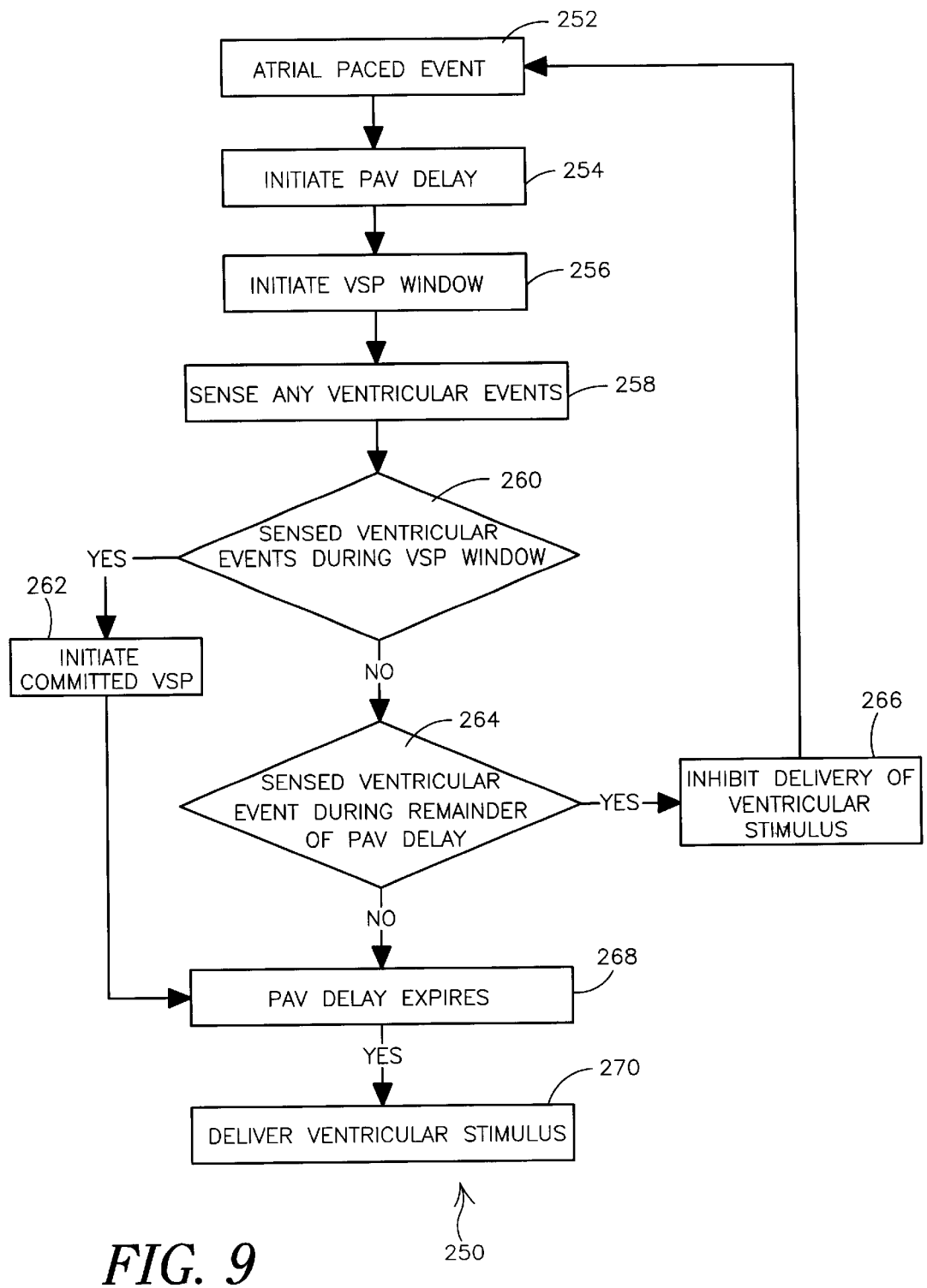
FIG. 9 is a flow diagram for use in describing ventricular safety pacing following an atrial paced event according to the present invention.

FIGS. 8 and 9 shall be used to describe VSP according to the present invention. FIG. 8 shows a VSP method 220 following the occurrence of an atrial sensed event (block 222), whereas FIG. 9 shows a VSP method 250 following the occurrence of an atrial paced event (block 252). An AV delay may be initiated by occurrence of either an atrial sensed event (block 222, see FIG. 8) or an atrial paced event (block 252, see FIG. 9). The AV delay is a programmed time period whose length is varied depending upon whether the AV delay is initiated by the occurrence of the atrial sensed event (block 222) or is initiated by the occurrence of an atrial paced event (block 252). Although the present method is described relative to VSP following both the occurrence of atrial sensed events and atrial paced events, it will be recognized that the present invention may also be limited to one or the other. In other words, a VSP feature may be turned on, programmed on, or enabled for just paced sensed events or VSP may be turned on, programmed on, or enabled for just atrial sensed events. However, preferably, according to the present invention, VSP is enabled for and occurs following both atrial sensed events and atrial paced events.

As shown in FIG. 8, upon the occurrence of an atrial sensed event (block 222), an SAV delay 203 is initiated (block 224). In addition, as shown in block 226, a VSP window 204 is defined during the initial portion of the SAV delay 203. During the SAV delay 203, sensing circuitry provides for the sensing of ventricular events (block 228). For example, ventricular activity or ventricular sensed events 206 (which may be false sense events resulting from cross talk, lead dislodgement, etc.) may be sensed during VSP window 204.

As the ventricular chambers are being monitored for ventricular events, if ventricular events are detected during VSP window 204 (block 230), such detected ventricular events initiate committed VSP (block 232). Once committed VSP is initiated (block 232), then upon expiration of SAV delay (block 238), a VSP ventricular pace is delivered (block 240).

If no ventricular events are sensed during the VSP window (block 230), the ventricular chambers are still being monitored for intrinsic activity. As such, ventricular events may be sensed during the remainder portion of the SAV interval (block 234).

If a ventricular event is sensed during the remainder portion of the SAV interval (block 234) and no ventricular events were detected during the VSP window 204, delivery of ventricular stimulus at the termination of the SAV delay 203 is inhibited (block 236). In such a circumstance, pacing is unnecessary as proper depolarization of the ventricle has occurred intrinsically. In other words, an intrinsic ventricular event controls heart activity. Such intrinsic activity controlling the heart is desirable.

If, however, a sensed ventricular event is not detected during the remainder (i.e., time portion 211) of the SAV interval (block 234) and no ventricular events were detected during the VSP window 204, then upon expiration of the SAV delay (block 238), ventricular stimulus is delivered (block 240).

In summary, and with reference to FIG. 7, ventricular stimulus is delivered 207 upon expiration of the SAV delay 203 if no ventricular events are sensed during the VSP window 204 defined during the initial portion of the SAV delay 203 and the remainder portion 211 thereof. If ventricular activity or events 206 are sensed during the VSP window, these events commit the pacemaker to the delivery of (and do not inhibit delivery of) ventricular stimulus upon expiration of the SAV delay 203. In such a manner, committed ventricular pacing therapy is provided at optimized and programmed SAV delay 203. However, if a ventricular event is sensed during the remainder portion 211 of the SAV interval 203 and no ventricular events were detected during the VSP window 204, delivery of ventricular stimulus at the termination of the SAV delay 203 is inhibited, e.g., intrinsic activity controls.

As shown in FIG. 9, upon the occurrence of an atrial paced event (block 252), a PAV delay 202 is initiated (block 254). In addition, as shown in block 256, a VSP window 204 is defined during the initial portion of the PAV delay 202. During the PAV delay 202, sensing circuitry provides for the sensing of ventricular events (block 258). For example, ventricular activity or ventricular sensed events 206 (which may be false sense events resulting from cross talk, lead dislodgement, etc.) may be sensed during VSP window 204.

As the ventricular chambers are being monitored for ventricular events, if ventricular events are detected during VSP window 204 (block 260), such detected ventricular events initiate committed VSP (block 262). Once committed VSP is initiated (block 262), then upon expiration of PAV delay (block 268), a VSP ventricular pace is delivered (block 270).

If no ventricular events are sensed during the VSP window (block 260), the ventricular chambers are still being monitored for intrinsic activity. As such, ventricular events may be sensed during the remainder portion (i.e., time portion 213) of the PAV interval (block 264).

If a ventricular event is sensed during the remainder portion (i.e., time portion 213) of the PAV interval (block 264) and no ventricular events were detected during the VSP window 204, delivery of ventricular stimulus at the termination of the PAV delay 202 is inhibited (block 266). In such a circumstance, pacing is unnecessary as proper depolarization of the ventricle has occurred intrinsically. In other words, an intrinsic ventricular event controls heart activity. Such intrinsic activity controlling the heart is desirable.

If, however, a sensed ventricular event is not detected during the remainder of the PAV interval (block 264) and no ventricular events were detected during the VSP window 204, then upon expiration of the PAV delay (block 268), ventricular stimulus is delivered (block 270).

In summary, and with reference to FIG. 7, ventricular stimulus is delivered 209 upon expiration of the PAV delay 202 if no ventricular events are sensed during the VSP window 204 defined during the initial portion of the PAV delay 202 and the remainder portion 213 thereof. If ventricular activity or events 206 are sensed during the VSP window, these events commit the pacemaker to the delivery of (and do not inhibit delivery of) ventricular stimulus upon expiration of the PAV delay 202. In such a manner, committed ventricular pacing therapy is provided at optimized and programmed PAV delay 202. However, if a ventricular event is sensed during the remainder portion 213 of the PAV interval 202 and no ventricular events were detected during the VSP window 204, delivery of ventricular stimulus at the termination of the PAV delay 202 is inhibited, e.g., intrinsic activity controls.

Figures 10A, 10B:
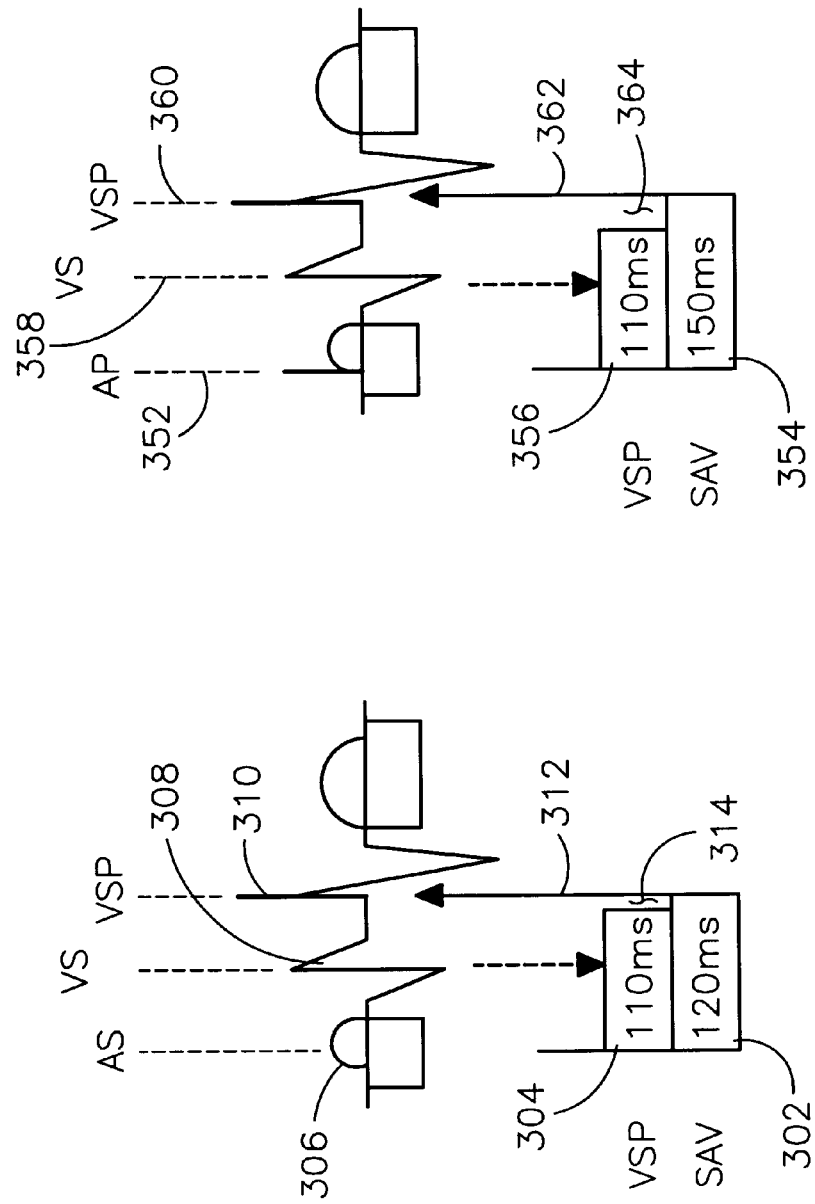
FIGS. 10A–10B illustrate examples of the delivery of ventricular safety pacing stimulus at optimized or programmed SAV and PAV intervals according to the present invention.

FIGS. 10A and 10B provide two illustrative examples of VSP for an SAV interval (as shown in FIG. 10A) and for a PAV interval (as shown in FIG. 10B). FIG. 10A shows a SAV delay 302 of 120 milliseconds initiated upon the occurrence of an atrial sensed event 306. Also upon occurrence of the atrial sensed event 306, VSP window 304 of 110 milliseconds is defined with a remainder period 314 subsequent thereto in the SAV delay 302. A ventricular event 308 is sensed during the VSP window 304. As such, this sensed ventricular event 308 commits the pacing apparatus to deliver a VSP pulse 310 at the termination 312 of the SAV interval or delay 302.

Likewise, FIG. 10B, shows a PAV delay 354 of 150 milliseconds initiated upon the occurrence of an atrial paced event 352. Also upon occurrence of the atrial paced event 352, VSP window 356 of 110 milliseconds is defined with a remainder period 364 subsequent thereto in the PAV delay 354. A ventricular event 358 is sensed during the VSP window 356. As such, this sensed ventricular event 358 commits the pacing apparatus to deliver a VSP pulse 360 at the termination 362 of the PAV interval or delay 354.

All patents and references cited herein are incorporated in their entirety as if each were incorporated separately. This invention has been described with reference to illustrative embodiments and is not meant to be construed in a limiting sense. As described previously, one skilled in the art will recognize that various other illustrative applications including, but not limited to, bi-ventricular pacing, may utilize the VSP techniques described herein. Various modifications of the illustrative embodiments, as well as additional embodiments of the invention, will be apparent to persons skilled in the art upon reference to this description.

What is claimed is:

1. A method of pacing for use in a medical device, the method comprising:
   providing a sensed AV delay following an atrial sensed event, wherein the sensed AV delay is a predetermined time period initiated by the atrial sensed event;
   defining a ventricular safety pacing window during at least an initial portion of the sensed AV delay, wherein the sensed AV delay further comprises a remainder portion thereof subsequent to the initial portion;
   sensing ventricular events during the sensed AV delay;
   delivering ventricular stimulus upon expiration of the sensed AV delay if no ventricular events are sensed during the ventricular safety pacing window defined during the initial portion of the sensed AV delay and the remainder portion thereof;
   inhibiting the delivery of ventricular stimulus upon expiration of the sensed AV delay if no ventricular events are sensed during the ventricular safety pacing window but a ventricular event is sensed during the remainder portion of the sensed AV delay; and
   committing to the delivery of a ventricular stimulus upon expiration of the sensed AV delay if a ventricular event is sensed during the ventricular safety pacing window.

2. The method of claim 1, wherein the sensed AV delay is equal to or greater than the ventricular safety pacing window.

3. The method of claim 1, wherein the ventricular safety pacing window during the initial portion of the sensed AV delay is 110 milliseconds.

4. The method of claim 1, wherein the method further comprises:
   providing a paced AV delay following an atrial paced event, wherein the paced AV delay is a predetermined time period initiated by the atrial paced event;
   defining a ventricular safety pacing window during at least an initial portion of the paced AV delay, wherein the paced AV delay further comprises a remainder portion thereof subsequent to the initial portion;
   sensing ventricular events during the paced AV delay;
   delivering ventricular stimulus upon expiration of the paced AV delay if no ventricular events are sensed during the ventricular safety pacing window defined during the initial portion of the paced AV delay and the remainder portion thereof;
   inhibiting the delivery of ventricular stimulus upon expiration of the paced AV delay if no ventricular events are sensed during the ventricular safety pacing window but a ventricular event is sensed during the remainder portion of the paced AV delay; and
   committing to the delivery of a ventricular stimulus upon expiration of the paced AV delay if a ventricular event is sensed during the ventricular safety pacing window.

5. The method of claim 4, wherein the ventricular safety pacing window during the initial portion of the paced AV delay is 110 milliseconds.

6. The method of claim 4, wherein the paced AV delay is equal to or greater than the ventricular safety pacing window.

7. The method of claim 4, wherein the ventricular safety pacing window during the initial portion of the paced AV delay is the same as the ventricular safety pacing window during the initial portion of the sensed AV delay.

8. The method of claim 4, wherein the paced AV delay and the sensed AV delay are both greater than the ventricular safety pacing window.

9. The method of claim 8, wherein the paced AV delay is greater than the sensed AV delay.

10. The method of claim 4, wherein the ventricular safety pacing window during the initial portion of the paced AV delay and the ventricular safety pacing window during the initial portion of the sensed AV delay are both 110 milliseconds.

11. The method of claim 1, wherein delivering ventricular stimulus comprises delivering bi-ventricular stimulus.

12. The method of claim 1, wherein the medical device is an implantable medical device.

13. The method of claim 12, wherein the implantable medical device includes an implantable medical device selected from one of a pacemaker, a defibrillator, a pacemaker/cardioverter/defibrillator, and a cardioverter/defibrillator.

14. A method of pacing for use in a medical device, the method comprising:
   providing an AV delay initiated by occurrence of either an atrial sensed event or an atrial paced event, wherein the AV delay is a programmed time period whose length is varied depending upon whether the AV delay is initiated by the occurrence of an atrial sensed event or is initiated by the occurrence of an atrial paced event;
   defining a ventricular safety pacing window during at least an initial portion of the AV delay;
   sensing ventricular events during the AV decay;
   delivering ventricular stimulus upon expiration of the AV delay if no ventricular events are sensed during the AV delay; and
   committing to the delivery of ventricular stimulus upon expiration of the AV delay if a ventricular event is sensed during the ventricular safety pacing window.

15. The method of claim 14, wherein the method further comprises inhibiting delivery of ventricular stimulus upon expiration of the AV delay if a ventricular event is not sensed during the ventricular safety pacing window but a ventricular event is sensed during a subsequent portion of the AV interval.

16. The method of claim 14, wherein providing the AV delay includes providing a sensed AV delay initiated by occurrence of an atrial sensed event or providing a paced AV delay initiated by occurrence of an atrial paced event.

17. The method of claim 16, wherein the ventricular safety pacing window during the initial portion of the paced AV delay and the ventricular safety pacing window during the initial portion of the sensed AV delay are 110 milliseconds.

18. The method of claim 16, wherein the paced AV delay and the sensed AV delay are both greater than the ventricular safety pacing window.

19. The method of claim 16, wherein the paced AV delay is greater than the sensed AV delay.

20. The method of claim 14, wherein delivering ventricular stimulus comprises delivering bi-ventricular stimulus.

21. The method of claim 14, wherein the medical device is an implantable medical device.

22. The method of claim 14, wherein the implantable medical device comprises an implantable medical device selected from one of a pacemaker, a defibrillator, a pacemaker/cardioverter/defibrillator, and a cardioverter/defibrillator.

23. A method of pacing in a dual chamber pacing apparatus, the method comprising:
providing a sensed AV delay following an atrial sensed event, wherein the sensed AV delay is a predetermined time period initiated by the atrial sensed event;
defining a ventricular safety pacing window during at least an initial portion of the sensed AV delay; and
committing to the delivery of a ventricular stimulus upon expiration of the sensed AV delay if a ventricular event is sensed during the ventricular safety pacing window, wherein the method further comprises:
delivering ventricular stimulus upon expiration of the sensed AV delay if no a ventricular events are sensed during the sensed AV delay; and
inhibiting the delivery of ventricular stimulus upon expiration of the sensed AV delay if no ventricular events are sensed during the ventricular safety pacing window but a ventricular event is sensed during a subsequent portion of the sensed AV delay.

24. A method of pacing in a dual chamber pacing apparatus, the method comprising:
providing a sensed AV delay following an atrial sensed event, wherein the sensed AV delay is a predetermined time period initiated by the atrial sensed event:
defining a ventricular safety pacing window during at least an initial portion of the sensed AV delay; and
committing to the delivery of a ventricular stimulus upon expiration of the sensed AV delay if a ventricular event is sensed during the ventricular safety pacing window, wherein the method further comprises:
providing a paced AV delay following an atrial paced event, wherein the paced AV delay is a predetermined time period initiated by the atrial paced event;
defining a ventricular safety pacing window during at least an initial portion of the paced AV delay; and
committing to the delivery of a ventricular stimulus upon expiration of the paced AV delay if a ventricular event is sensed during the ventricular safety pacing window thereof.

25. The method of claim 24, wherein the ventricular safety pacing window during the initial portion of the sensed AV delay is 110 milliseconds.

26. The method of claim 24, wherein the sensed AV delay is equal to or greater than the ventricular safety pacing window.

27. The method of claim 24, wherein the ventricular safety pacing window during the initial portion of the paced AV delay is 110 milliseconds.

28. The method of claim 24, wherein the paced AV delay is greater than the ventricular safety pacing window.

29. The method of claim 24, wherein the paced AV delay and the sensed AV delay are both greater than the ventricular safety pacing window.

30. The method of claim 29, wherein the paced AV delay is greater than the sensed AV delay.

31. The method of claim 24, wherein the ventricular safety pacing window during the initial portion of the paced AV delay and the ventricular safety pacing window during the initial portion of the sensed AV delay are both 110 milliseconds.

32. The method of claim 24, wherein delivering ventricular stimulus comprises delivering bi-ventricular stimulus.

33. The method of claim 24, wherein the dual chamber pacing apparatus comprises an implantable medical device selected from one of a pacemaker, a defibrillator, a pacemaker/cardioverter/defibrillator, and a cardioverter/defibrillator.

34. A dual chamber pacing apparatus, the apparatus comprising:
atrial pacing and sensing circuitry to generate atrial pacing pulses and sense atrial events;
ventricular pacing and sensing circuitry to generate ventricular pacing pulses and sense ventricular events; and
control circuitry operable to:
provide a sensed AV delay following an atrial sensed event detected using the atrial sensing circuitry, wherein the sensed AV delay is a predetermined time period initiated by the atrial sensed event;
define a ventricular safety pacing window during at least an initial portion of the sensed AV delay, wherein the sensed AV delay further comprises a remainder portion thereof subsequent to the initial portion;
detect ventricular events using the ventricular sensing circuitry during the sensed AV delay;
control delivery of ventricular stimulus using the ventricular pacing circuitry upon expiration of the sensed AV delay such that:
if no ventricular events are detected during the ventricular safety pacing window defined during the initial portion of the sensed AV delay and the remainder portion thereof then ventricular stimulus is delivered at the expiration of the sensed AV delay;
if a ventricular event is not detected during the ventricular safety pacing window but a ventricular event is detected during the remainder portion of the sensed AV delay then delivery of ventricular stimulus upon expiration of the sensed AV delay is inhibited; and
if a ventricular event is sensed by the ventricular sensing circuitry during the ventricular safety pacing window then the ventricular pacing circuitry is committed to delivery of ventricular stimulus upon expiration of the sensed AV delay.

35. The apparatus of claim 34, wherein the ventricular safety pacing window during the initial portion of the sensed AV delay is 110 milliseconds.

36. The apparatus of claim 34, wherein the sensed AV delay is equal to or greater than the ventricular safety pacing window.

37. The apparatus of claim 34, wherein the control circuitry is further operable to:
provide a paced AV delay following an atrial paced event, wherein the paced AV delay is a predetermined time period initiated by the occurrence of an atrial paced event associated with the generation of atrial pacing pulses by the atrial pacing circuitry;

define a ventricular safety pacing window during at least an initial portion of the paced AV delay, wherein the paced AV delay further comprises a remainder portion thereof subsequent to the initial portion;

detect ventricular events during the paced AV delay;

control delivery of ventricular stimulus using the ventricular pacing circuitry upon expiration of the paced AV delay such that:
- if no ventricular events are detected during the ventricular safety pacing window defined during the initial portion of the paced AV delay and the remainder portion thereof then ventricular stimulus is delivered at the expiration of the paced AV delay;
- if a ventricular event is not detected during the ventricular safety pacing window but a ventricular event is detected during the remainder portion of the paced AV delay then delivery of ventricular stimulus upon expiration of the paced AV delay is inhibited; and
- if a ventricular event is sensed by the ventricular sensing circuitry during the ventricular safety pacing window then the ventricular pacing circuitry is committed to delivery of ventricular stimulus upon expiration of the paced AV delay.

38. The apparatus of claim 37, wherein the ventricular safety pacing window during the initial portion of the paced AV delay is 110 milliseconds.

39. The apparatus of claim 37, wherein the paced AV delay is greater than the ventricular safety pacing window.

40. The apparatus of claim 37, wherein the ventricular safety pacing window during the initial portion of the paced AV delay is the same as the ventricular safety pacing window during the initial portion of the sensed AV delay.

41. The apparatus of claim 37, wherein the paced AV delay and the sensed AV delay are both greater than the ventricular safety pacing window.

42. The apparatus of claim 41, wherein the paced AV delay is greater than the sensed AV delay.

43. The apparatus of claim 37, wherein the ventricular safety pacing window during the initial portion of the paced AV delay and the ventricular safety pacing window during the initial portion of the sensed AV delay are both 110 milliseconds.

44. The apparatus of claim 37, wherein ventricular pacing and sensing circuitry comprises bi-ventricular pacing and sensing circuitry to generate bi-ventricular pacing pulses and sense ventricular events.

45. The apparatus of claim 34, wherein the dual chamber pacing apparatus comprises an implantable medical device selected from one of a pacemaker, a defibrillator, a pacemaker/cardioverter/defibrillator, and a cardioverter/defibrillator.

46. A dual chamber pacing apparatus, the apparatus comprising: atrial pacing and sensing circuitry to generate atrial pacing pulses and sense atrial events; ventricular pacing and sensing circuitry to generate ventricular pacing pulses and sense ventricular events; and control circuitry operable to:
- provide an AV delay initiated by occurrence of either an atrial sensed event detected by the atrial sensing circuitry or an atrial paced event associated with the generation of atrial pacing pulses using the atrial pacing circuitry, wherein the AV delay is a programmed time period whose length is varied depending upon whether the AV delay is initiated by the occurrence of an atrial sensed event or is initiated by the occurrence of an atrial paced event;
- define a ventricular safety pacing window during at least an initial portion of the AV delay;
- detect ventricular events during the AV delay; and
- commit to delivery of ventricular stimulus by the ventricular pacing circuitry upon expiration of the AV delay if a ventricular event is sensed by the ventricular sensing circuitry during the ventricular safety pacing window.

47. The apparatus of claim 46, wherein the control circuitry is further operable to:
- initiate delivery of ventricular stimulus using the ventricular pacing circuitry upon expiration of the AV delay if no ventricular events are sensed during the AV delay; and
- inhibit the delivery of ventricular stimulus upon expiration of the AV delay if a ventricular event is not sensed during the ventricular safety pacing window but a ventricular event is sensed during a subsequent portion of the AV delay.

48. The apparatus of claim 46, wherein the control circuitry is further operable to provide a sensed AV delay initiated by occurrence of an atrial sensed event or provide a paced AV delay initiated by occurrence of an atrial paced event.

49. The apparatus of claim 48, wherein the ventricular safety pacing window during the initial portion of the paced AV delay and the ventricular safety pacing window during the initial portion of the sensed AV are both 110 milliseconds.

50. The apparatus of claim 48, wherein the paced AV delay and the sensed AV delay are both greater than the ventricular safety pacing window.

51. The apparatus of claim 48, wherein the paced AV delay is greater than the sensed AV delay.

52. The apparatus of claim 46, wherein ventricular pacing and sensing circuitry comprises bi-ventricular pacing and sensing circuitry to generate bi-ventricular pacing pulses and sense ventricular events.

53. The apparatus of claim 46, wherein the dual chamber pacing apparatus comprises an implantable medical device selected from one of a pacemaker, a defibrillator, a pacemaker/cardioverter/defibrillator, and a cardioverter/defibrillator.

* * * * *